United States Patent
Cully et al.

(10) Patent No.: US 9,526,503 B2
(45) Date of Patent: Dec. 27, 2016

(54) LUMBAR OSTIA OCCLUSION DEVICES AND METHODS OF DEPLOYING THE SAME

(71) Applicant: W. L. Gore & Associates, Inc., Newark, DE (US)

(72) Inventors: Edward H. Cully, Flagstaff, AZ (US); Jeffrey B. Duncan, Flagstaff, AZ (US); Douglas S. Paget, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 13 days.

(21) Appl. No.: 14/456,897

(22) Filed: Aug. 11, 2014

(65) Prior Publication Data

US 2015/0045872 A1 Feb. 12, 2015

Related U.S. Application Data

(60) Provisional application No. 61/865,036, filed on Aug. 12, 2013.

(51) Int. Cl.
*A61F 2/07* (2013.01)
*A61B 17/12* (2006.01)

(52) U.S. Cl.
CPC ... *A61B 17/12109* (2013.01); *A61B 17/12113* (2013.01); *A61B 17/12131* (2013.01); *A61B 17/12168* (2013.01)

(58) Field of Classification Search
CPC .................. A61F 2/06; A61F 2/00; A61F 2/07
USPC ................................................ 623/1.22–1.36
See application file for complete search history.

(56) References Cited

U.S. PATENT DOCUMENTS

| | | | | |
|---|---|---|---|---|
| 5,100,422 A | * | 3/1992 | Berguer | A61B 17/0057 411/339 |
| 5,634,895 A | * | 6/1997 | Igo | A61M 25/10 604/20 |
| 5,665,117 A | | 9/1997 | Rhodes | |
| 5,910,168 A | * | 6/1999 | Myers | A61L 27/507 623/1.44 |
| 8,118,856 B2 | | 2/2012 | Schreck et al. | |
| 8,469,873 B2 | * | 6/2013 | Miller | A61B 17/12 600/16 |
| 2004/0098096 A1 | * | 5/2004 | Eton | A61F 2/07 623/1.13 |
| 2006/0052866 A1 | * | 3/2006 | Gilles | A61B 17/12013 623/1.51 |
| 2006/0155041 A1 | * | 7/2006 | Suzuki | A61L 17/12 524/492 |

(Continued)

OTHER PUBLICATIONS

Duarte, A.P.; Coelho, J.F.; Bordado, J.C.; Cidade, M.T.; Gil, M.H. Surgical adhesives: Systematic review of the main types and development forecast. Progress in Polymer Science: 2012; 37: 1031-1050.

(Continued)

*Primary Examiner* — Suzette J Gherbi (57) ABSTRACT

A lumbar occluding device or patch is disclosed for reducing Type II endoleaks in connection with endovascular aneurysm repair (EVAR) of aortic aneurisms. The lumbar occluding patch can be applied to a vessel wall and, more particularly, the posterior wall of the aortic artery in the location of the abdominal aneurysm to block or occlude an array of lumbar artery ostia concurrent with or following a stent graft deployment in an EVAR procedure.

12 Claims, 10 Drawing Sheets

(56) References Cited

U.S. PATENT DOCUMENTS

| | | | | |
|---|---|---|---|---|
| 2007/0135677 | A1* | 6/2007 | Miller | A61B 17/12 600/37 |
| 2008/0188923 | A1* | 8/2008 | Chu | A61B 17/12118 623/1.15 |
| 2008/0228259 | A1* | 9/2008 | Chu | A61F 2/07 623/1.11 |
| 2009/0024152 | A1* | 1/2009 | Boyden | G06Q 50/22 606/155 |
| 2009/0287297 | A1* | 11/2009 | Cox | A61B 17/12022 623/1.22 |
| 2009/0318941 | A1* | 12/2009 | Sepetka | A61B 17/12022 606/158 |
| 2010/0256668 | A1* | 10/2010 | Perry, Jr. | A61B 17/1285 606/194 |
| 2010/0278893 | A1* | 11/2010 | Bodin | A61L 27/34 424/423 |
| 2013/0289587 | A1* | 10/2013 | Shalev | A61F 2/07 606/158 |
| 2013/0303842 | A1* | 11/2013 | Zeitels | A61L 27/3625 600/36 |
| 2014/0018937 | A1* | 1/2014 | Bosley, Jr. | A61L 27/3633 623/23.72 |
| 2014/0066979 | A1* | 3/2014 | Jonsson | A61B 17/0057 606/213 |
| 2015/0073523 | A1* | 3/2015 | Chobotov | A61L 31/022 623/1.11 |
| 2015/0313605 | A1* | 11/2015 | Griffin | A61B 17/12172 606/200 |

OTHER PUBLICATIONS

Creech, Jr. MD., O. Endo-aneurysmorrhaphy and Treatment of Aortic Aneurysm. Annals of Surgery: vol. 164; Dec. 1966, No. 6: 935-946.

Kallmes, D.F.; Ding, Y.H.; Dai D.; Kadirvel, R.; Lewis, D.A.; Cloft, H.J. A New Endoluminal, Flow-Disrupting Device for Treatment of Seccular Aneurysms. Stroke: 2007; 38: 2346-2352.

* cited by examiner

LUMBAR OSTIA OCCLUSION DEVICES AND METHODS OF DEPLOYING THE SAME

BACKGROUND

Field

The invention relates to medical devices for treating vascular disease and, more particularly, to endoluminally deliverable lumbar ostia occlusion devices and methods of deploying the same.

Discussion of the Related Art

An aortic aneurysm is a widening of the aorta usually as a result of a weakening of the aortic wall. Continued widening of an aortic aneurysm can result in formation of an aneurysm sac, which ultimately can rupture. Aortic aneurysms can be treated with open surgery or by endovascular aneurysm repair (EVAR) using a stent graft. In EVAR, a stent graft is delivered endoluminally to "exclude" the aortic aneurysm by bridging and allowing blood flow between healthy portions of the aorta on opposite ends of the aneurysm.

While exclusion of the aneurysm sac is a primary goal of the stent-graft treatment, it is known that leaks or "endoleaks" of varying degree can nonetheless still occur after deployment of the stent graft resulting in complications. An endoleak is defined as a persistent blood flow outside the lumen of the stent graft but within an aneurysm sac or adjacent vascular segment being treated by the stent graft. Increased blood flow into the aneurysm due to endoleaks can cause enlargement of the aneurysm sac, which can increase pressure and can cause rupture.

Endoleaks can result from incomplete sealing between the stent graft and aorta. Endoleaks can also result from persistent patency or blood flow into the aneurysm sac due to retrograde or opposing blood flow from collateral vessels, such as lumbar arteries, inferior mesenteric artery, and other aortic branches "excluded" by the stent graft. This latter type of endoleak is commonly referred to as a "Type II" endoleak.

Repair of Type II endoleaks is routinely done via a transarterial or translumbar approach. Initially, Type II endoleaks were treated by doing single-vessel embolization of the feeding artery using a microcatheter, wherein the collateral branch vessel supplying the endoleak was selectively embolized with coils near the aneurysm sac. Recurrence of endoleaks, however, following such procedures is common and believed to be due to multiple vessels feeding the endoleak. In other words, when one or some of the vessels are embolized, other vessels may continue to feed the endoleak into the aneurysm sac.

Another approach to repairing type II endoleaks is via a translumbar approach, which involves embolizing the endoleak sac nidus to break the communication between the multiple arteries that supply the endoleak. Other methods of treating Type II endoleaks includes ligation or clipping of the arteries of concern.

It remains desirable to provide an improved device and delivery of the same for treating endoleaks, particularly Type II endoleaks, following or in connection with EVA.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting.

Figure 1:
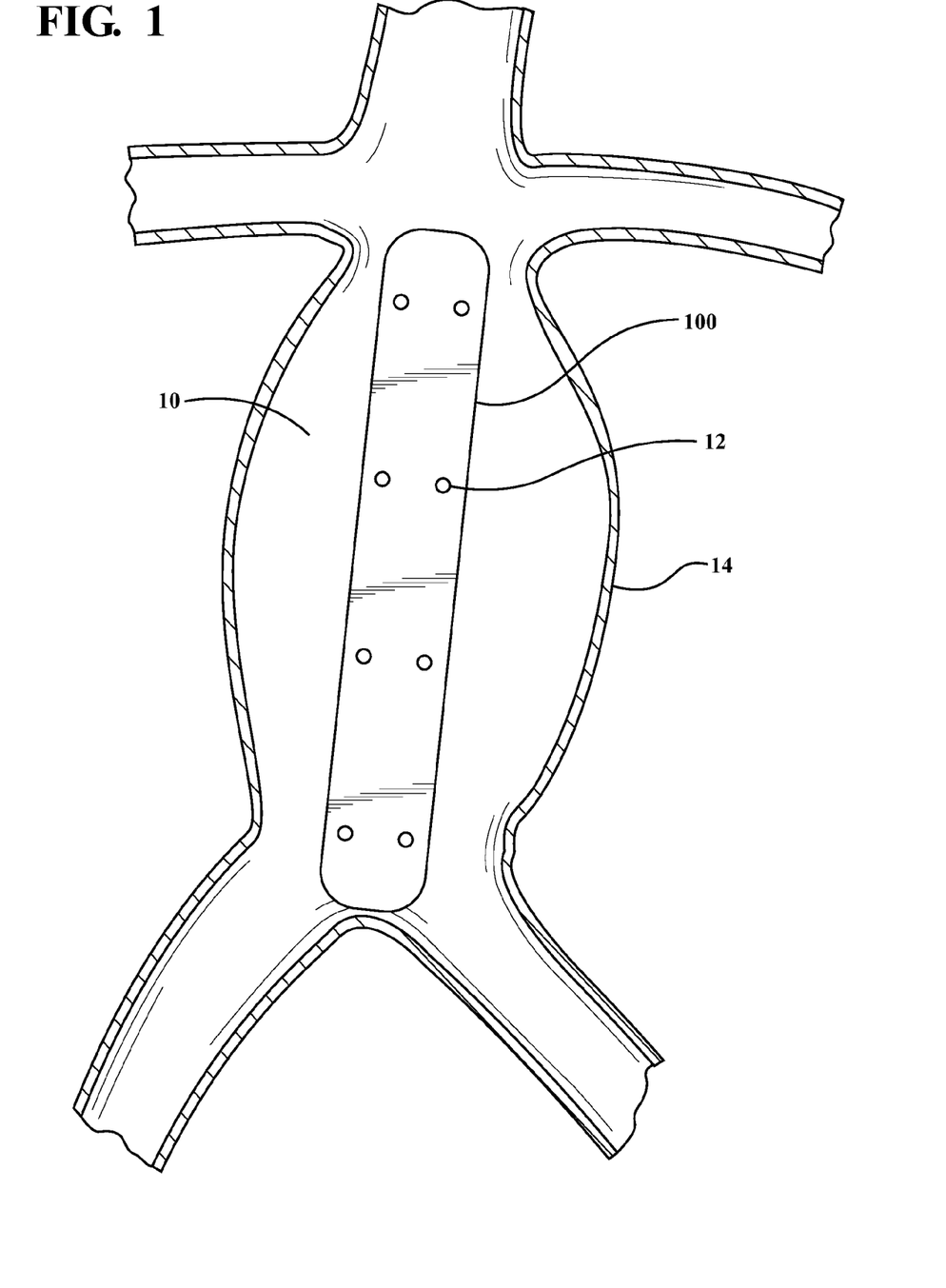
FIG. 1 is a front view of an aortic aneurysmal sac and a patch in accordance with various embodiments for occluding lumbar artery ostia in the aortic aneurysm sac.

In various embodiments, as shown for example in FIG. 1, a lumbar occluding device or patch is disclosed for reducing Type II endoleaks in connection with endovascular aneurysm repair (EVAR) of aortic aneurisms and indicated at 100. The lumbar occluding patch 100 can be applied to a vessel wall 10 and, more particularly, the posterior wall of the aortic artery in the location of the abdominal aneurysm 14 to block or occlude an array of lumbar artery ostia 12 concurrent with or following a stent graft deployment in an EVAR procedure.

The lumbar occluding patch can comprise any one or combination of biocompatible materials which can be formed to a suitable shape and thickness for occluding, and reducing or otherwise impeding blood flow through the array of lumbar artery ostia. The lumbar occluding patch can be formed from a film, weave, braid or other constructs of a polymer. In various embodiments, for example, a lumbar occluding patch can comprise one or more layers of one or a combination of film, weave, braid or other constructs of polymer.

Polymers for forming the patch can include any one or combination of polyester, polyurethane, fluoropolymers, such as perfouorelastomers and the like, polytetrafluoroethylene (PTFE), expanded PTFE, silicones, urethanes, ultra high molecular weight polyethylene, aramid fibers, high strength polymer fibers such as ultra high molecular weight polyethylene fibers (e.g., Spectra®, Dyneema Purity®, etc.) or aramid fibers (e.g., Technora®, etc.), or any combinations thereof. Other examples of biocompatible materials for constructing the lumbar occluding patch can include thin-film metals, such as Nitinol, aluminum, stainless steel and absorbable metals such as magnesium.

Figure 2:
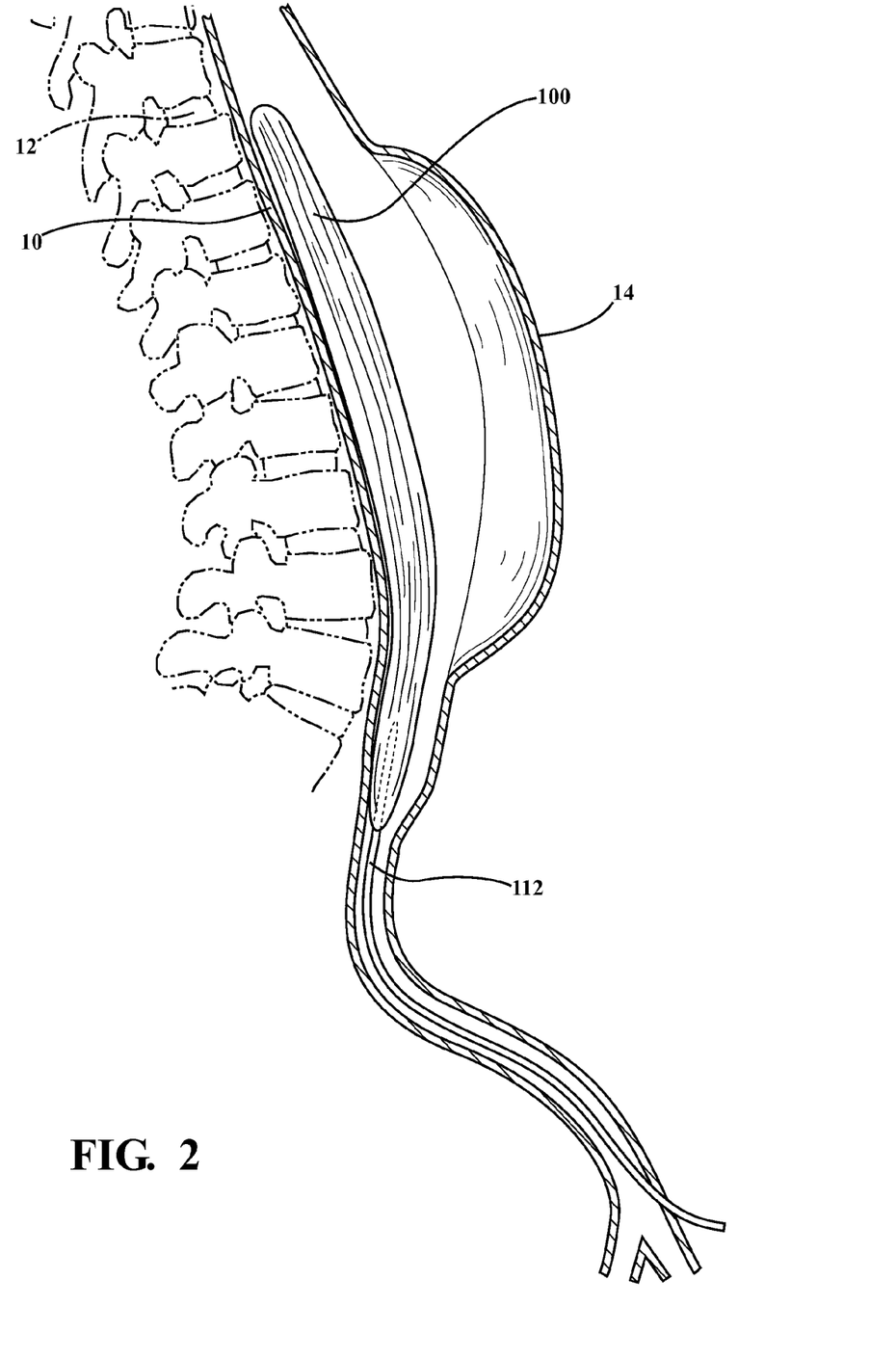
FIG. 2 is a side view of an aortic aneurysmal sac, a patch, in accordance with various embodiments, for occluding lumbar artery ostia in the aortic aneurysm sac, and a delivery system for endoluminal delivery of the patch to the aortic aneurysm sac.

In various embodiments, the lumbar occluding patch can be configured for endoluminal catheter delivery to a desired treatment site. In FIG. 2, for example, a lumbar occluding patch 100 can be compacted on an end of a catheter 112 for endoluminal delivery using a sheath, restraining member, or other arrangements for releasably maintaining the lumbar occluding device toward a compacted state for endoluminal delivery and deployment at the treatment site. The lumbar occluding patch and delivery system can be rendered radiopaque to allow visualization with fluoroscopy. General placement of the lumbar occluding patch will allow coverage of most of the lumbar arteries involved in the aneurysm and minimize the need to visualize them independently.

Figure 3:
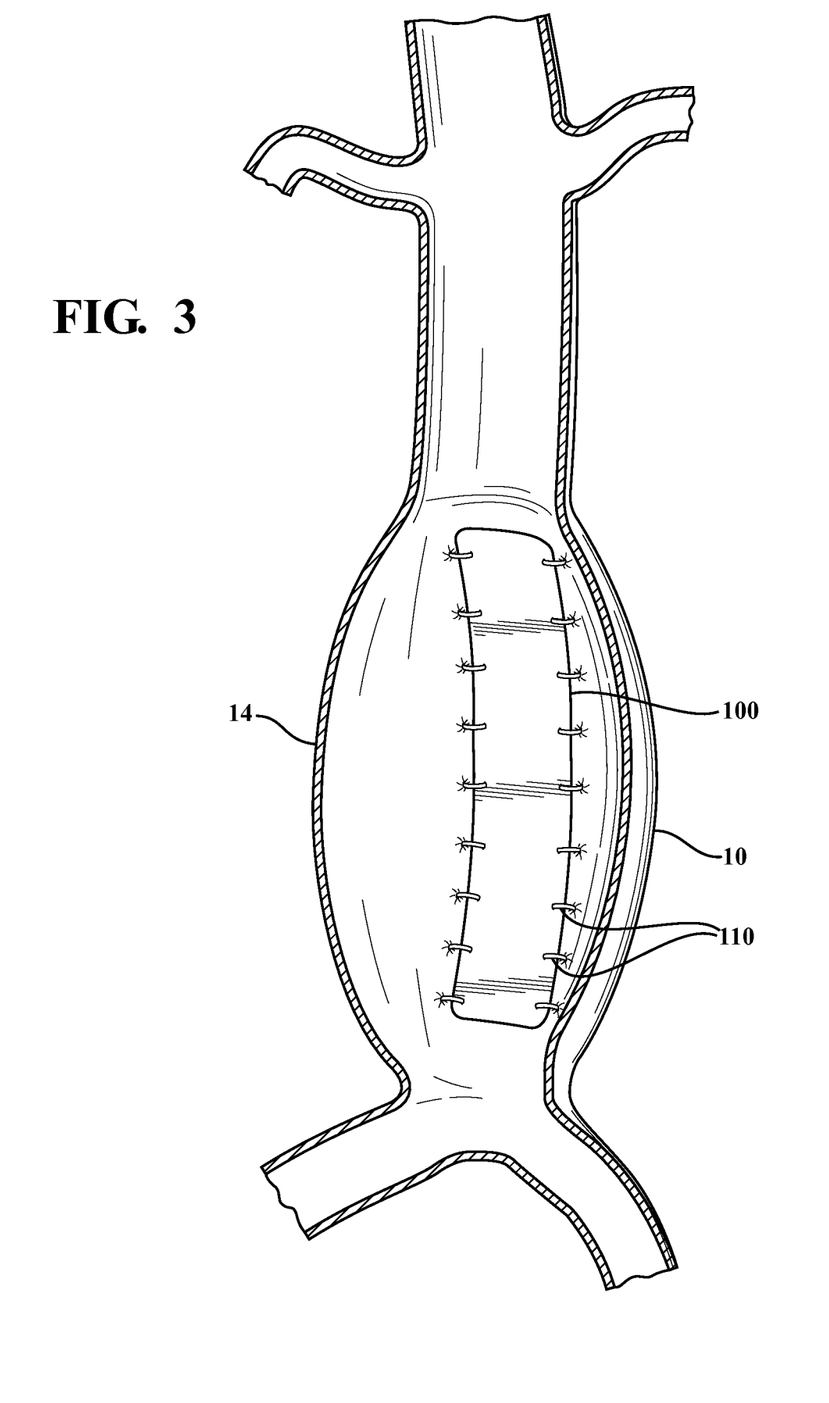
FIG. 3 is a front view of an aortic aneurysmal sac, a patch in accordance with various embodiments for occluding lumbar artery ostia in the aortic aneurysm sac, and an attachment arrangement for attaching the patch to the vessel wall.

In various embodiments, the patch can include a coupling mechanism disposed along at least portions of the surface for attaching the lumbar occlusion patch to the vessel wall. The coupling mechanism can comprise adhesives, hooks, anchors, barbs, and the like, or any combinations thereof. As illustrated in FIG. 3, for example, a patch 100 can be attached to the vessel wall 10 by a plurality of staples 110.

Figure 4A:
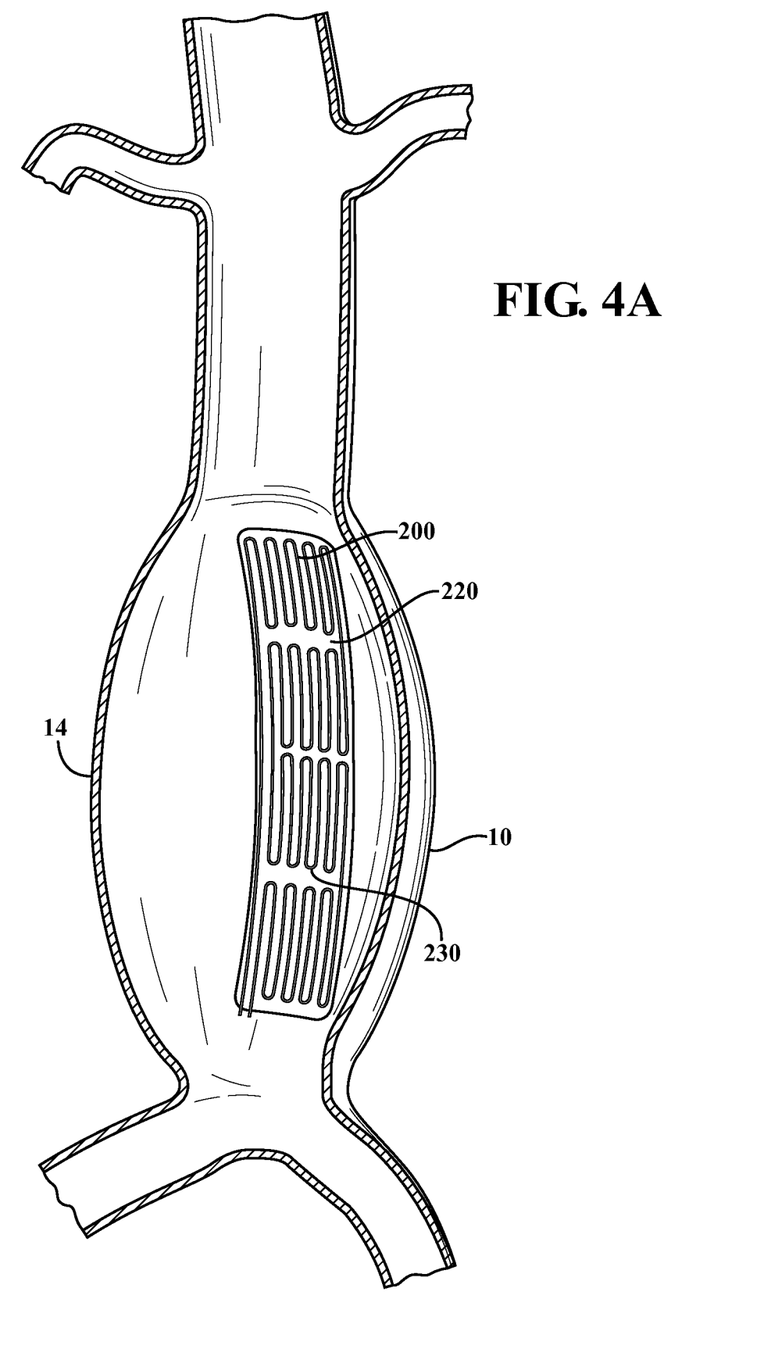
FIG. 4A is perspective view of an aortic aneurysmal sac and a patch in accordance with various embodiments for occluding lumbar artery ostia in the aortic aneurysm sac and having a heating element for promoting adhesion between the patch and the vessel walls of the aortic aneurysm sac.
Figure 4B:
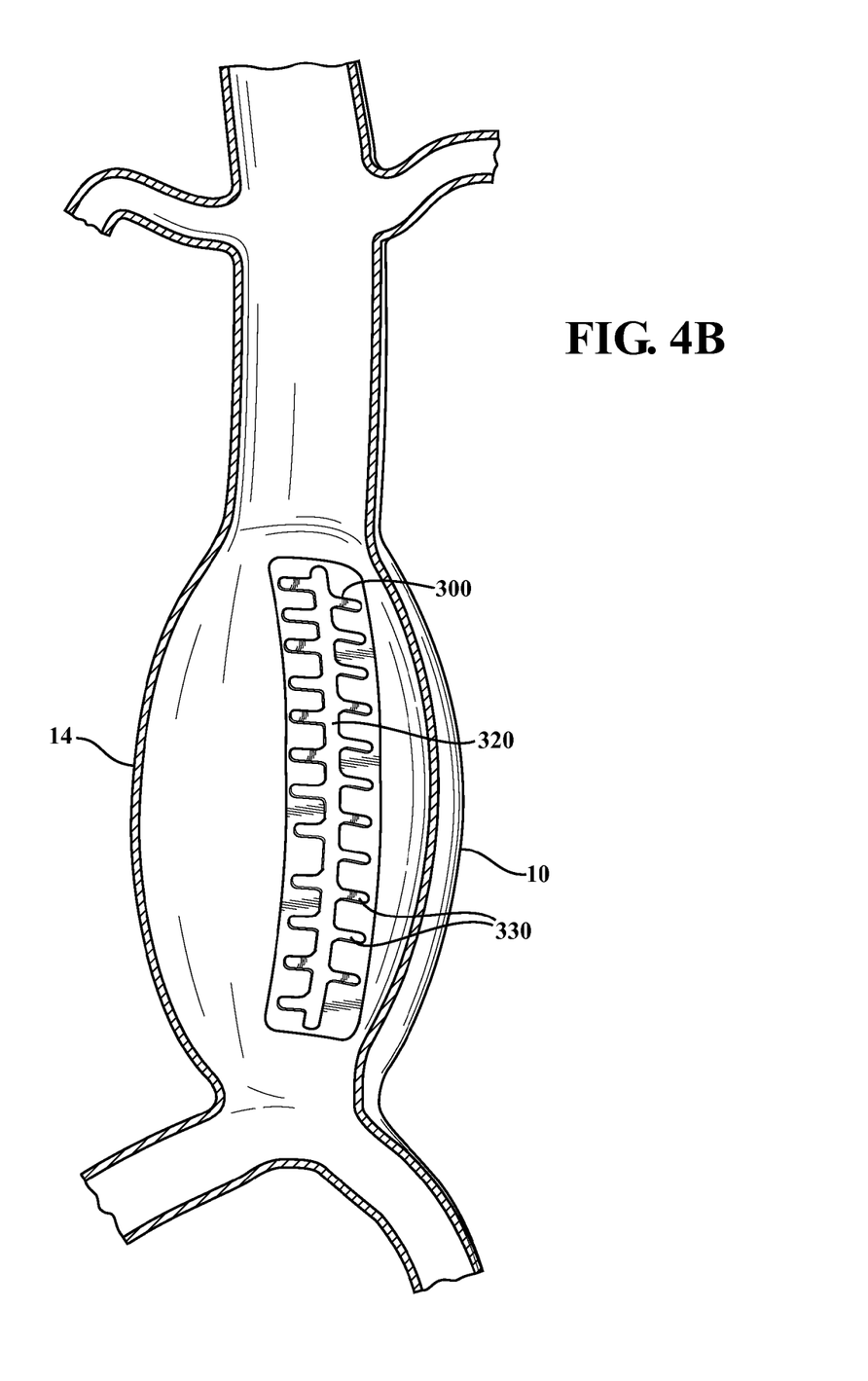
FIG. 4B is perspective view of an aortic aneurysmal sac and a patch in accordance with various embodiments for occluding lumbar artery ostia in the aortic aneurysm sac and incorporating a chemically-based heating arrangement for promoting adhesion between the patch and the vessel walls of the aortic aneurysm sac.

Referring to FIGS. 4A and 4B, lumbar occluding patches in accordance with various embodiments are generally indicated at 200 and 300, respectively. The patches 200, 300 can be delivered and secured along the vessel wall over the lumbar artery ostia. The patches 200, 300 can be flat and non-tubular, and can have a thickness of 0.10 mm or more. The patches 200, 300 can be made of multiple layers of any one or combination of constructs of biocompatible materials, as described above. The patches 200, 300 can be formed, in various embodiments, from one or more layers of ePTFE. The ePTFE, in such embodiments, can include microstructures configured for rapid cellular infiltration to facilitate acute adhesion and chronic tissue attachment and incorporation. An example of such an ePTFE film microstructure can be found in U.S. Pat. No. 5,814,405 to Branca.

The patches 200, 300 each have an abluminal surface 220, 320 for contacting a vessel wall 10. The patches 200, 300 can be configured to attach to the vessel wall 10. The abluminal surfaces 220, 320, for example, can include an adhesive disposed along at least a portion thereof for fixedly securing the lumbar occluding patch 200, 300 to the vessel wall. An adhesive for securing the lumbar occluding patch to the vessel wall can include suitable materials as listed in *Surgical adhesives: Systematic review of the main types and development forecast*, Progress in Polymer Science 2012;37: 1031-1050, Duarte A P, Coelho J F, Bordado J C, Cidade M T, Gil M H, the content of which is incorporated herein by reference.

Figure 7:
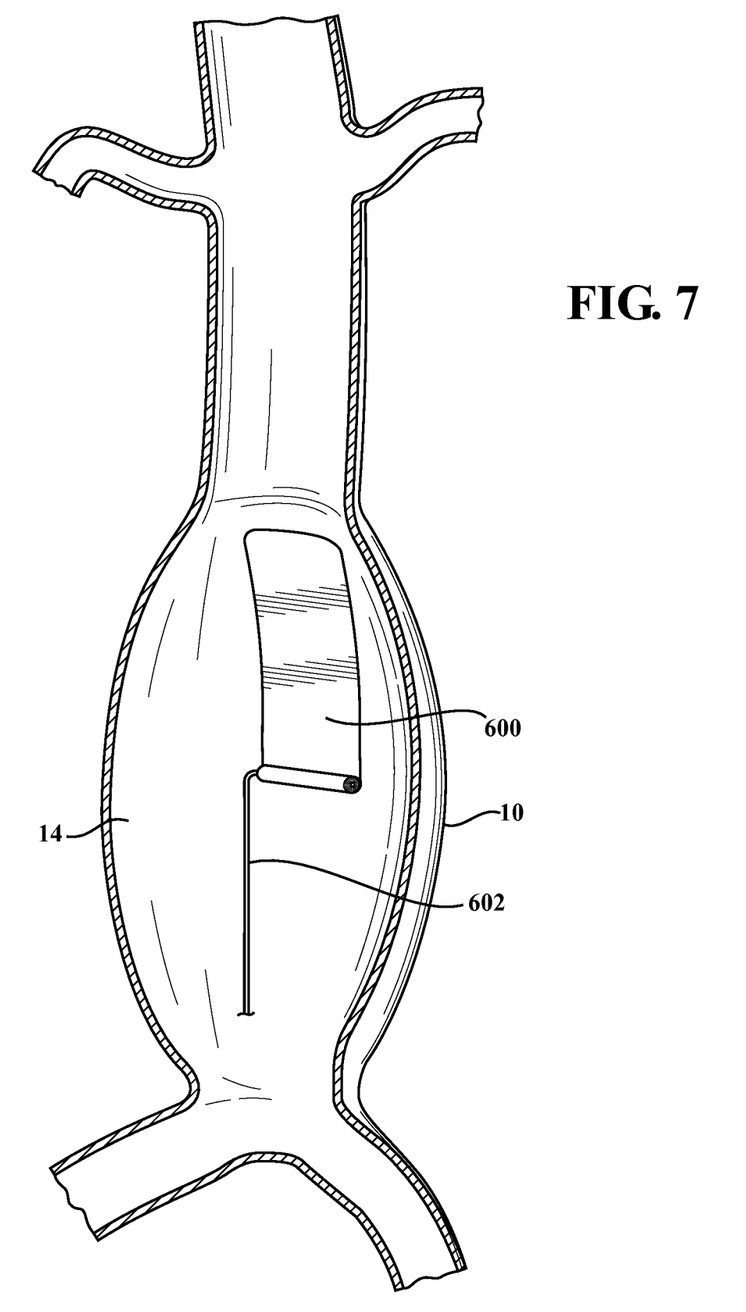
FIG. 7 is perspective view of an aortic aneurysmal sac, a patch for occluding lumbar artery ostia in the aortic aneurysm sac, and a tool for facilitating deployment of the patch, in accordance with various embodiments.

Energy, such as thermal, UV, laser, ultrasonic and RF, can be used to activate an adhesive and promote adhesion of the lumbar artery occlusion device to the vessel wall. Activation of an adhesive can be done prior to implantation of the lumbar artery occlusion device or peri-operatively in situ. Other arrangements for attaching the lumbar occluding patch to the vessel wall can include anchors, staples, sutures and the like. The patch, alternatively, can be formed from any suitable biocompatible self-adhering material. Pressure can be applied to facilitate attachment of the patch to the vessel wall. A roller 602, for example as shown in FIG. 7 and described in greater detail below, can be delivered endoluminally via a catheter based system concurrent with or following delivery of a patch 600 to the treatment site and used to apply pressure along the patch 600 to promote adhesion or attachment of the patch 600 to the vessel wall 10.

A lumbar occluding patch in accordance with various embodiments can also include a support structure coupled thereto or otherwise integral therewith for maintaining or biasing the lumbar occluding patch toward a desired shape and/or conformance with the vessel wall. The support structure can have various configurations such as a wire, flat, twisted, lattice, weave, or any combinations thereof. A support structure for a lumbar occluding patch can be formed from any one or combination of polymeric, metallic or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; and metals such as stainless steels, cobalt-chromium alloys, nitinol, or thin-sheet versions thereof; and biologically derived materials such as bovine arteries/veins, pericardium and collagen; or any combination thereof.

A patch formed from one or more layers of a polymer construct, in a number of embodiments, can include a support structure secured along a surface of the one or more layers of polymer construct or sandwiched between an adjacent pair of the one or more layers of polymer construct. Thus, a support structure can, for example, include a wire or thin-film metal frame which can be attached to a surface of a layer or sandwiched between adjacent layers of a patch to maintain or bias the patch toward a desired shape or toward conformance with the vessel wall. Alternatively, a patch can include one or more layers of ePTFE film and a Nitinol frame structure disposed along a surface of the one or more layers of ePTFE film or sandwiched between adjacent layers of ePTFE.

In various embodiments, a patch can be formed from one or more layers of polymer, and a support structure can be defined by selectively densified regions in the polymer itself. Densification of the polymer can be achieved by any methods known by those having ordinary skill in the art, such as by localized heat and/or pressure. A patch can, for example, be formed from one or more layers of ePTFE and a support structure can be defined by selectively densified regions in the ePTFE itself.

The lumbar occluding patch and/or the support structure can also comprise bioresorbable materials such as poly (amino acids), poly(anhydrides), poly(caprolactones), poly (lactic/glycolic acid) polymers, poly(hydroxybutyrates) and poly(orthoesters).

Referring to FIG. 4A, a patch 200 in accordance with various embodiments can comprise one or more layers of any one or combination of polymer films, such as ePTFE. A metallic heating element 230 can be embedded along a surface of the one or more layers or between adjacent pairs of the one or more layers. During delivery, the heating element 230 can be selectively electrically energized to produce a prescribed amount of heat to the vessel wall, which can promote clotting in the lumbar arteries or at the ostia thereof, as well as promote adhesion of the patch to the vessel wall, particularly where adhesives are used to attach the patch to the vessel wall.

In various embodiments, as shown illustratively in FIG. 4B, a patch 300 can be configured with a chemical-based heating arrangement to generate heat by including a substance that will generate heat when a catalyst is applied to it, such as Zeolite. Zeolite generates heat when exposed to liquid, such as blood. Zeolite can, for example, be "quilted" between layers of ePTFE, as indicated at 330. The ePTFE can be rendered hydrophilic, so as to facilitate passive "wetting" or passing of blood components therethrough to hydrate the Zeolite and thereby generate heat. Alternatively, the Zeolite can be be encased within impermeable layers of ePTFE and selectively hydrated by injection of saline through a dedicated lumen in fluid communication with the Zeolite. Other substances known by those having ordinary skill in the art which generate heat by passive or selective exposure to a catalyst can also be utilized.

Figure 5A:
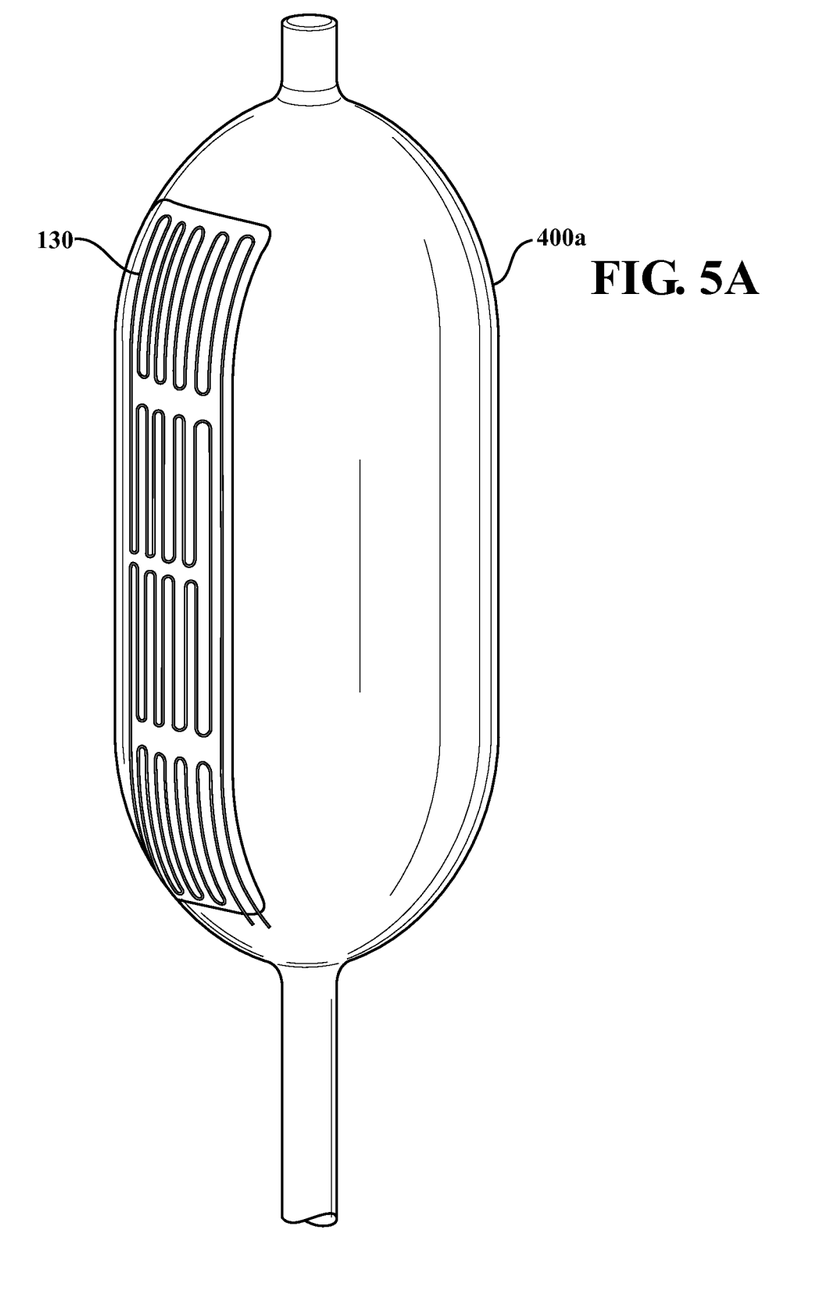
FIG. 5A is a perspective view of a balloon for pressing a patch toward the vessel walls of the aortic aneurysm sac and having a heating element for promoting adhesion between the patch and the vessel walls of the aortic aneurysm sac, in accordance with various embodiments.
Figure 5B:
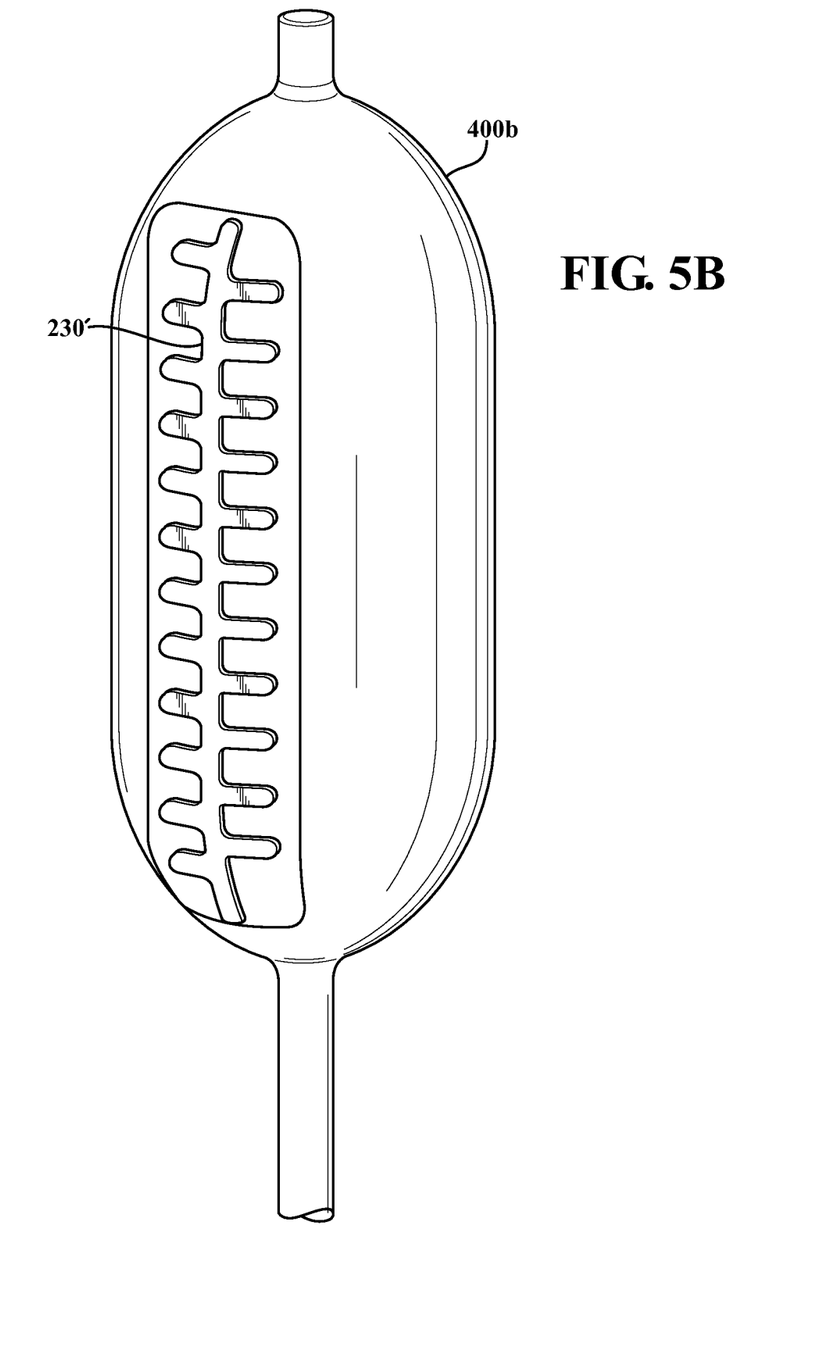
FIG. 5B is a perspective view of a balloon for pressing a patch toward the vessel walls of the aortic aneurysm sac and incorporating a chemically-based heating arrangement for promoting adhesion between the patch and the vessel walls of the aortic aneurysm sac, in accordance with various embodiments.
Figure 6A:
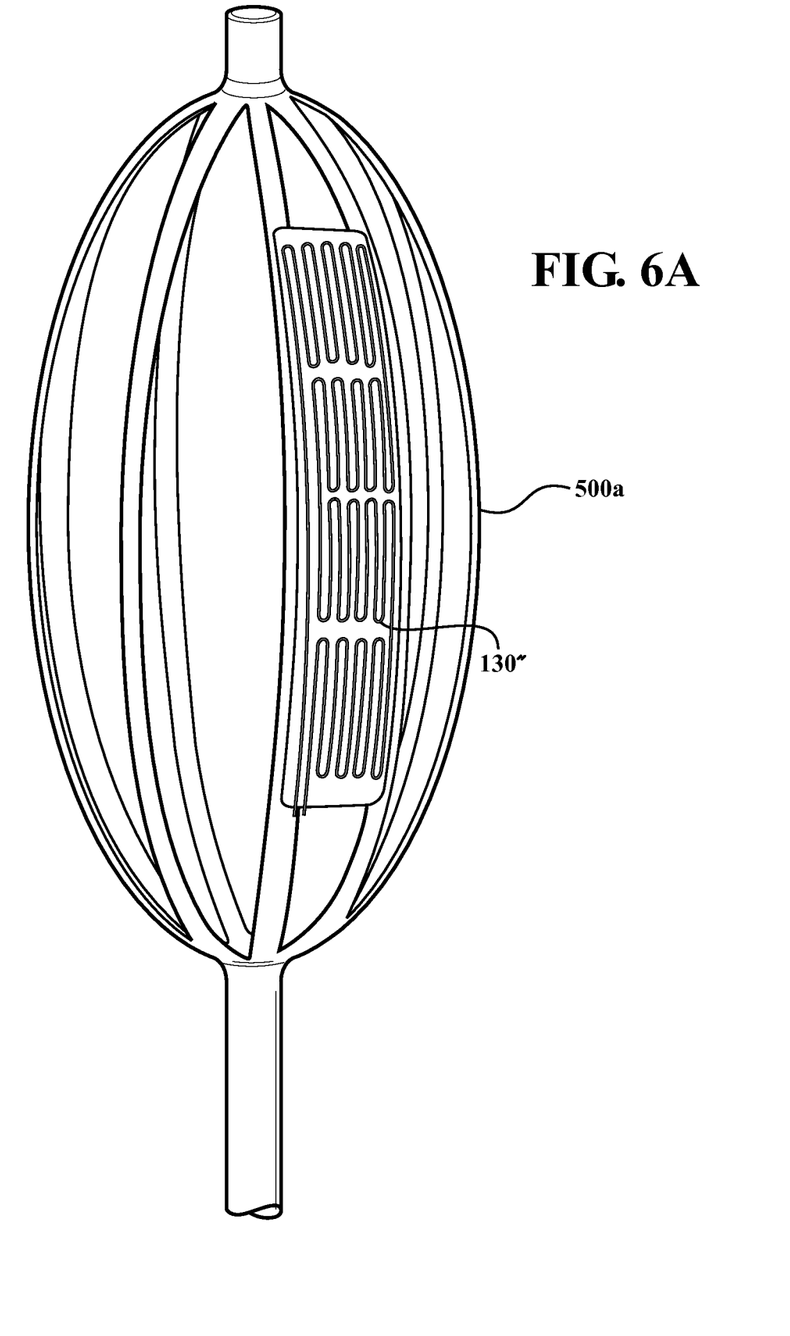
FIG. 6A is a perspective view of a mechanical balloon for pressing a patch toward the vessel walls of the aortic aneurysm sac and including a heating element for promoting adhesion between the patch and the vessel walls of the aortic aneurysm sac, in accordance with various embodiments.
Figure 6B:
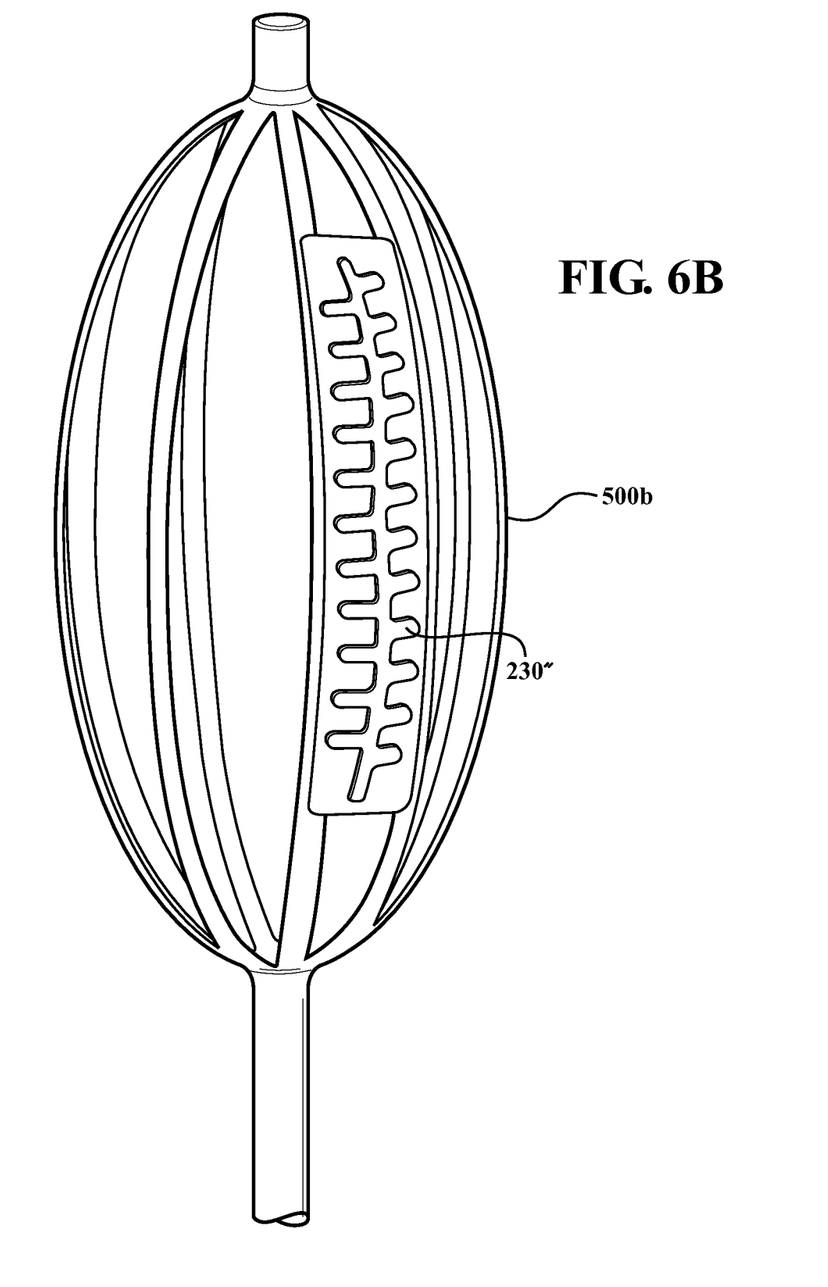
FIG. 6B is a perspective view of a mechanical balloon for pressing a patch toward the vessel walls of the aortic aneurysm sac and incorporating a chemically-based heating arrangement for promoting adhesion between the patch and the vessel walls of the aortic aneurysm sac, in accordance with various embodiments.

In other embodiments and in connection with the delivery system, both electrical and chemical methods of heat generation for promoting clotting and/or adhesion can be configured as part of the delivery system rather than the device, as described above. The delivery system can be configured to include a hydraulically activated balloon 400a, 400b, for example as illustrated in FIGS. 5A and 5B, respectively, or a mechanically actuated balloon 500a, 500b, for example as illustrated in FIGS. 6A and 6B, respectively. A metallic heating element 130', 130" can be integrated with either of the hydraulically 400a or mechanically 500a activated balloons. Similarly, either of the hydraulically 400b or mechanically 500b activated balloons can include a chemically-based heating arrangement utilizing a "quilted" structure 230', 230", as earlier described, for storing a substance that will generate heat when a catalyst is applied to it, such as Zeolite. In either cases, a balloon can be expanded to apply sufficient pressure on the patch and hold it securely against the posterior wall of the aorta for a prescribed time. For example, if a suitable adhesive is applied along an abluminal surface of a patch, the balloon can be inflated to press the patch against the vessel wall until desired adhesion is achieved. The patch will remain attached to the vessel wall after deflating or minimizing the balloon profile.

The patch may be temporarily attached to the delivery system with any suitable bio-absorbable adhesive, such as polyglycolic acid (PGA), PGA/trimethylenecarbonate copolymers (PGA/TMC), polylactic acid (PLA), PLA/PGA, poly-L-lactic acid (PLLA), poly-DL-lactic acid (PDLLA), poly-p-dioxanone (PDS) and poly-beta-hydroxybutyric acid (PBHBA). When heat is generated, the bio-absorable adhesive will release the patch. Additional heat will promote adhesion between adhesive applied along the abluminal surface of the patch and the vessel wall. By this arrangement, the patch can be transferred from the delivery system to the vessel wall. The delivery system can be sufficiently marked with RO identifiers to facilitate accurate placement of the patch both longitudinally and rotationally at the treatment site.

Referring back to FIG. 7, a delivery system in accordance with various embodiments can be configured to apply a lumbar occlusion patch onto to the vessel wall. More specifically, the delivery system can include a roller 602 for applying pressure onto a lumbar occlusion patch 600 to promote adhesion or attachment of the patch to the vessel wall 10. The roller can be formed from shape memory metal, such as Nitinol. The roller, in a non-deployed configuration, can be housed within a lumen of a catheter used for protecting and deploying the ePTFE patch. Upon deployment, the shape memory roller can be displaced from the lumen of the catheter and assume a generally orthogonal configuration, as shown in FIG. 7. In the deployed state, the roller can provide a necessary amount of pressure to apply the patch and hold it securely for a prescribed time. One benefit of keeping the patch in a rolled configuration is that the patch is protected during the procedure assuring that the patch does not "wet out" prior to the application. Another benefit is that a patch can be pre-coated or pre-impregnated with a desired therapeutic agent, such as a sclerosant, and in the rolled configuration remain wet with the therapeutic agent during the procedure. This ensures a maximum amount of the therapeutic agent is delivered at a desired moment and location during the procedure. The delivery system can be sufficiently marked with RO identifiers to allow accurate placement both longitudinally and rotationally.

In various embodiments, patches can include bioabsorbable materials alone or in combination with ePTFE, as disclosed, for example, in U.S. Pat. No. 7,655,584 and U.S. Pat. No. 7,659,219. Suitable polymeric materials for the bioabsorbable support member include, but are not limited to a block co-polymer of polyglycolic acid and trimethylene carbonate (PGA/TMC), polylactic acid/polyglycolic acid (PLA/PGA), or other homopolymers, copolymers, or polymeric blends derived from other biocompatible bioabsorbable monomeric components. Such homopolymers, copolymers or polymeric blends can be comprised of varying amounts of one or more of the following monomer examples: glycolide, d,l-lactide, l-lactide, d-lactide, p-dioxanone (1,4-dioxane-2-one), trimethylene carbonate (1,3-dioxane-2-one), .epsilon.-caprolactone, gamma.-butyrolactone, delta.-valerolactone, 1,4-dioxepan-2-one, and 1,5-dioxepan-2-one. Other bioabsorbable polymeric constituents may include ethylene glycol, propylene glycol, n-vinyl pyrrolidone, amino acids, anhydrides, orthoesters, phosphazines, amides, urethanes, and phosphoesters. Alternative copolymers may possess, in whole or in part, combinations of block, segmented, random, alternating, or statistical polymeric construction characteristics.

In particular embodiments, the patch can include a semi-crystalline segmented block copolymer of 67% PGA:33% TMC. The ratios of the PGA/TMC constituents can be adjusted during synthesis to alter the mechanical strength, bioabsorption rates, and processability of the co-polymer. Of particular significance with respect to the present disclosure is the ability of PGA/TMC co-polymers to change in shape from a compacted, or rolled, configuration to an uncompacted, or flattened, configuration without undergoing a thermal transition. Accordingly, devices in accordance with the present disclosure can be introduced, self-expanded, or unraveled, and secured at a range of human body temperatures.

Patches in accordance with other embodiments can be configured for use in closing other side-branch sites and anatomical apertures such as atrial septal defects, ventricular septal defects, an entry site to a saccular aneurysm such as found in the cranial vascular system, focal aortic defects, entry sites to pseudo aneurysms, entry tears to aortic dissections, and also defects, natural or man-made within the gastro-intestinal system, such as full section biopsy or polyp removal sites.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of reducing type II endoleaks in an aortic aneurismal sac, said method comprising:
   locate and identify treatment site;
   deliver and position a lumbar artery occlusion device configured for conforming to the infrarenal posterior abdominal aortic wall using a catheter-based delivery system;
   deploy the lumbar occlusion device;
   attach the lumbar artery occlusion device to the infrarenal posterior abdominal aortic wall;
   retract delivery system; and
   deploy an abdominal aortic aneurism exclusion (AAA) device, wherein the abdominal aortic aneurism is delivered and deployed to the treatment site separately from the lumbar occlusion device.

2. The method as set forth in 1, wherein the treatment site includes one or more lumbar artery ostia and the path is deployed to cover the one or more lumbar artery ostia.

3. The method as set forth in 1, wherein the lumbar artery occlusion device has a planar configuration.

4. The method as set forth in 1, wherein the attachment of the lumbar artery occlusion device to the infrarenal posterior abdominal aortic wall includes anchors, hooks, barbs, adhesives, applications of energy (thermal, UV, laser, ultrasonic, RF) to promote adhesion of the lumbar artery occlusion device to vessel, and/or self-adhering material.

5. The method as set forth in 1, wherein the lumbar artery occlusion device includes a radiopaque marker.

6. The method as set forth in 1, wherein the lumbar artery occlusion device is non-tubular.

7. The method as set forth in 1 including pressing the patch toward the vessel wall to promote attachment of the lumbar artery occlusion device to the vessel wall.

8. The method as set forth in 1, wherein the lumbar artery occlusion device is deployed after the AAA device.

9. The method as set forth in 1 including providing adhesive for attaching the lumbar artery occlusion device to the infrarenal posterior abdominal aortic wall.

10. The method as set forth in 9, wherein the adhesive is activated prior to implantation of lumbar occlusion device.

11. The method as set forth in 10, wherein an activator for activating adhesive is applied to vessel wall prior to implantation of lumbar occlusion device.

12. A method of reducing type II endoleaks in an aortic aneurismal sac, said method comprising:
   provide a lumbar artery occlusion device for reducing type II endoleaks in an aortic aneurismal sac, said device comprising a patch that is flat and non-tubular, the patch having an abluminal surface for contacting a vessel wall along the aortic aneurismal sac to occlude one or more lumbar artery ostia, the patch configured to attach to the vessel wall;
   locate and identify treatment site;
   deliver and position the lumbar artery occlusion device;
   deploy the lumbar occlusion device;
   attach the lumbar artery occlusion device to the infrarenal posterior abdominal aortic wall;
   retract delivery system; and
   deploy an abdominal aortic aneurism exclusion (AAA) device, wherein the abdominal aortic aneurism is delivered and deployed to the treatment site separately from the lumbar occlusion device.

* * * * *

UNITED STATES PATENT AND TRADEMARK OFFICE
CERTIFICATE OF CORRECTION

PATENT NO. : 9,526,503 B2
APPLICATION NO. : 14/456897
DATED : December 27, 2016
INVENTOR(S) : Edward H. Cully, Jeffrey B. Duncan and Douglas S. Paget Page 1 of 1

It is certified that error appears in the above-identified patent and that said Letters Patent is hereby corrected as shown below:

In the Claims

In Column 7, Claim 2, replace "as set forth in 1," with --as set forth in claim 1,--

In Column 7, Claim 3, replace "as set forth in 1," with --as set forth in claim 1,--

In Column 7, Claim 4, replace "as set forth in 1," with --as set forth in claim 1,--

In Column 8, Claim 5, replace "as set forth in 1," with --as set forth in claim 1,--

In Column 8, Claim 6, replace "as set forth in 1," with --as set forth in claim 1,--

In Column 8, Claim 7, replace "as set forth in 1," with --as set forth in claim 1,--

In Column 8, Claim 8, replace "as set forth in 1," with --as set forth in claim 1,--

In Column 8, Claim 9, replace "as set forth in 1," with --as set forth in claim 1,--

In Column 8, Claim 10, replace "as set forth in 9," with --as set forth in claim 9,--

In Column 8, Claim 11, replace "as set forth in 10," with --as set forth in claim 10,--

Signed and Sealed this
Eighteenth Day of June, 2019

Andrei Iancu
*Director of the United States Patent and Trademark Office*